(12) United States Patent
Bautista et al.

(10) Patent No.: US 6,331,432 B1
(45) Date of Patent: Dec. 18, 2001

(54) DEVICE AND METHOD FOR CLEANING AND SANITIZING A FOOD RESERVOIR

(75) Inventors: Derrick Bautista, Sherman; David Collins-Thompson, New Milford, both of CT (US)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/613,722

(22) Filed: Jul. 11, 2000

(51) Int. Cl.⁷ .................................................. D06M 16/00
(52) U.S. Cl. ............................ 435/264; 134/8; 134/25.4; 134/26; 134/29; 134/42
(58) Field of Search .................................. 435/264, 283.1, 435/286.5; 134/99.2, 6, 8, 22.17, 22.19, 25.4, 26, 29, 42; 510/111, 218, 219, 234, 321, 392, 406

(56) References Cited

U.S. PATENT DOCUMENTS

| | | | |
|---|---|---|---|
| 5,205,304 | * | 4/1993 | Cooper et al. . |
| 5,316,688 | | 5/1994 | Gladfelter et al. ..................... 252/90 |
| 5,932,171 | * | 8/1999 | Malchesky .............................. 422/29 |

* cited by examiner

Primary Examiner—David A. Redding
(74) Attorney, Agent, or Firm—Winston & Strawn

(57) ABSTRACT

A device for cleaning and sanitizing a food reservoir. The device includes two parts. The first part contains at least one or more enzymes and the second part contains one or more antimicrobial agents. The second part is isolated from the first part by a degradable barrier that is solid and stable under storage conditions but is adapted to decompose upon exposure to the aqueous conditions used for cleaning.

20 Claims, 3 Drawing Sheets

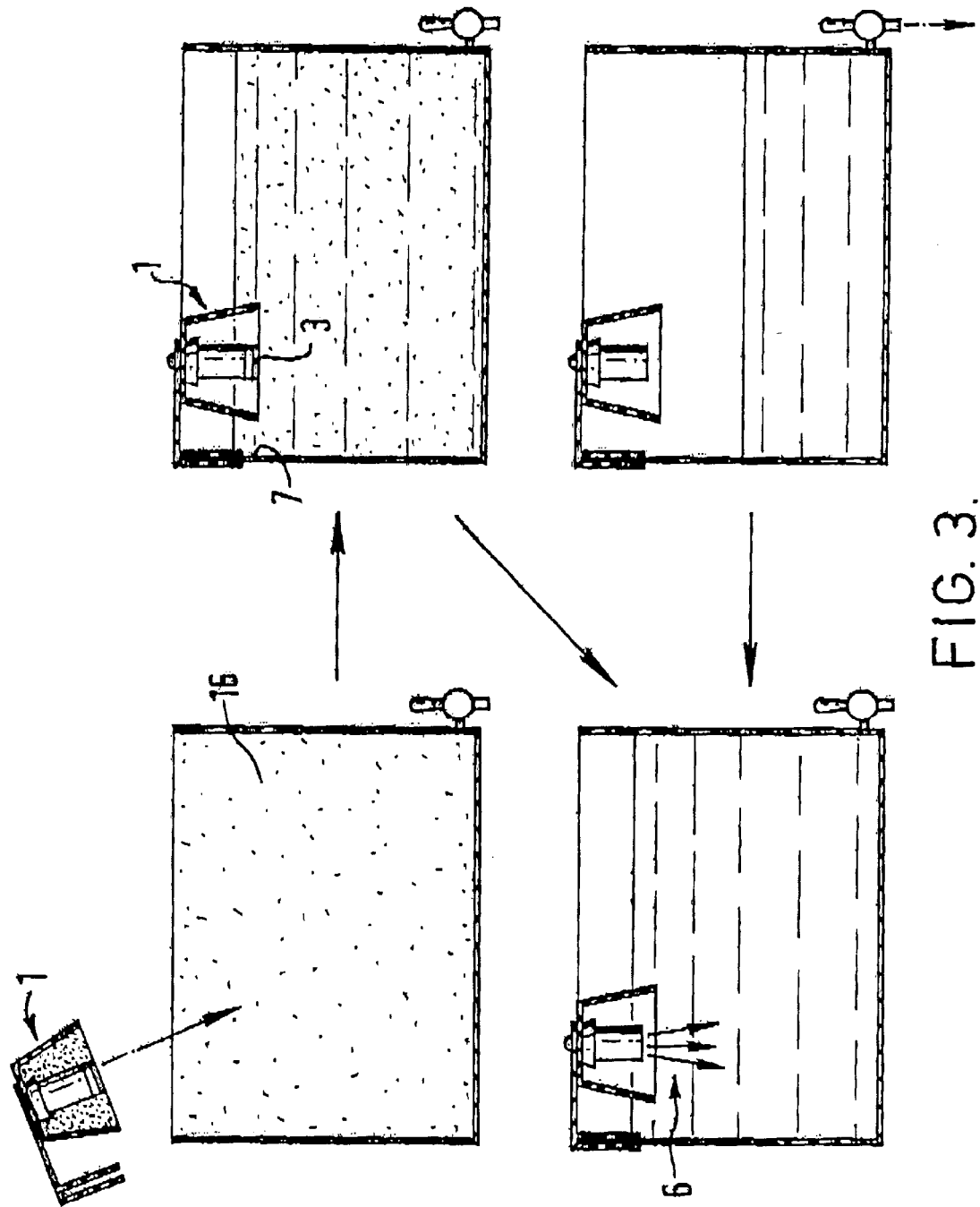

DEVICE AND METHOD FOR CLEANING AND SANITIZING A FOOD RESERVOIR

FIELD OF THE INVENTION

The present invention relates to a device for use in cleaning and sanitizing the reservoirs of food dispensing systems.

BACKGROUND OF THE INVENTION

Reservoirs in food dispensing systems, in particular beverage dispensers, require regular cleaning and sanitizing. Often, the reservoirs have translucid or transparent walls to enable the beverage or food to be displayed. These walls have a tendency to become opaque because of food debris and sediment being progressively deposited thereon and must be cleaned. These deposits can be difficult to remove with conventional detergents. The reservoir must also be microbiologically safe to prevent any risks of food contamination. Known methods to clean and sanitize beverage reservoirs rely mainly upon labor intensive activity by an individual. In most cases, the reservoir of a beverage-dispensing device must be taken apart and manually cleaned with a detergent and water. The reservoir is then rinsed with water and disinfected with an appropriate sanitizing solution before the unit is reassembled. Depending upon the amount of soil found on the surfaces of the reservoir, the time required to clean and sanitize a reservoir may take from 30 minutes to more than an hour. Also, the operator who performs the cleaning and sanitizing procedure must dedicate his/her time to this task and therefore becomes unavailable for other more valuable duties.

U.S. Pat. No. 5,316,688 relates to an alkaline cleaning system containing an alkaline detergent composition and an alkali stable continuous polymeric film that is soluble or dispersible in water that covers the alkaline detergent composition and prevents the operator from being exposed to the composition prior to use. The composition is in the form of a block or tablet that is dissolved in a single cleaning phase. The formulation, however, can only include active cleaning agents that are compatible when they are combined together in the block. This limits the use of combinations of very active cleaning and/or sanitizing substances.

There is a need for improved cleaning and sanitizing procedures for food and beverage reservoirs. To date, little has been done to simplify and/or reduce the amount of labor required to clean and sanitize these types of systems.

SUMMARY OF THE INVENTION

The invention is directed to a device and a process for cleansing and sanitizing a beverage or food reservoir. The device includes a first compartment that contains a cleaning component that includes at least one or more enzymes in an amount sufficient to cleanse the reservoir, a second compartment containing at least one antimicrobial substance in an amount sufficient to sanitize the reservoir. The second compartment is enclosed within a barrier that degrades when it contacts an aqueous medium to delay the release of the antimicrobial substance from the second compartment until after the cleaning component has cleansed the reservoir.

The degradable barrier may be soluble in the aqueous medium. The aqueous medium-soluble degradable barrier may include one or more layers with at least one layer being a sugar-based material. The degradable barrier may have a first outer layer made of the sugar-based material and a second inner support layer made of a second material, wherein the first material dissolves more slowly in the aqueous medium than the second material and the second inner support layer is more rigid than the first layer. The second inner layer may be effervescent. The barrier may include at least one layer capable of being degraded by one or more of the enzymes included in the first compartment after the one or more enzymes are released into the aqueous medium. The barrier comprises a protein capable of being degraded by a protease or a polysaccharide capable of being degraded by an amylase.

The first compartment may include at least one opening to dispense the cleaning component into the reservoir by gravity when the device is positioned in the reservoir so that the opening is directed downward. The device may further include a removable lid, attached to the opening, that prevents the cleaning component from exiting the opening until after the lid is removed. The device may include means for hanging the device on the edge of the reservoir so that the opening faces downward. In one embodiment the first compartment is defined by the walls of a housing and the walls of an inner tube that is attached to the housing, the second compartment is defined by the interior of the inner tube, and the barrier is exposed to and can contact the aqueous medium after the lid is removed.

The cleaning component may also include one or more detergents selected from the group consisting of alkali metal hydroxides, carbonates, silicates, phosphates, sulfites, and mixtures thereof. The one or more enzymes of the cleaning component may be an amylase, a protease, a lipases, or a mixture thereof. The antimicrobial agent may be chlorine or a quaternary ammonium compound.

The barrier may be adapted to release the antimicrobial composition into the reservoir after about 15 to 40 minutes following the release of the detergent, preferably about 25 to 35 minutes following the release of the detergent.

The invention is also directed to a method for cleaning and sanitizing a beverage or food reservoir. The method involves filling the reservoir with water; placing the device of the invention in the reservoir so that the cleaning component is released from the first compartment, the barrier is at least partially immersed in the water, and the antimicrobial substance is released from the second compartment after the barrier degrades to cleanse and sanitize the reservoir; and draining the water solution after the antimicrobial agent has sanitized the reservoir.

The device may be placed in the reservoir for about 30 to 60 minutes or preferably for about 25 to 45 minutes.

BRIEF DESCRIPTION OF THE DRAWINGS

FIG. 3 is an illustration of the method for cleaning and sanitizing a reservoir in accordance with the device of the invention.

DETAILED DESCRIPTION OF THE INVENTION

Figure 1:
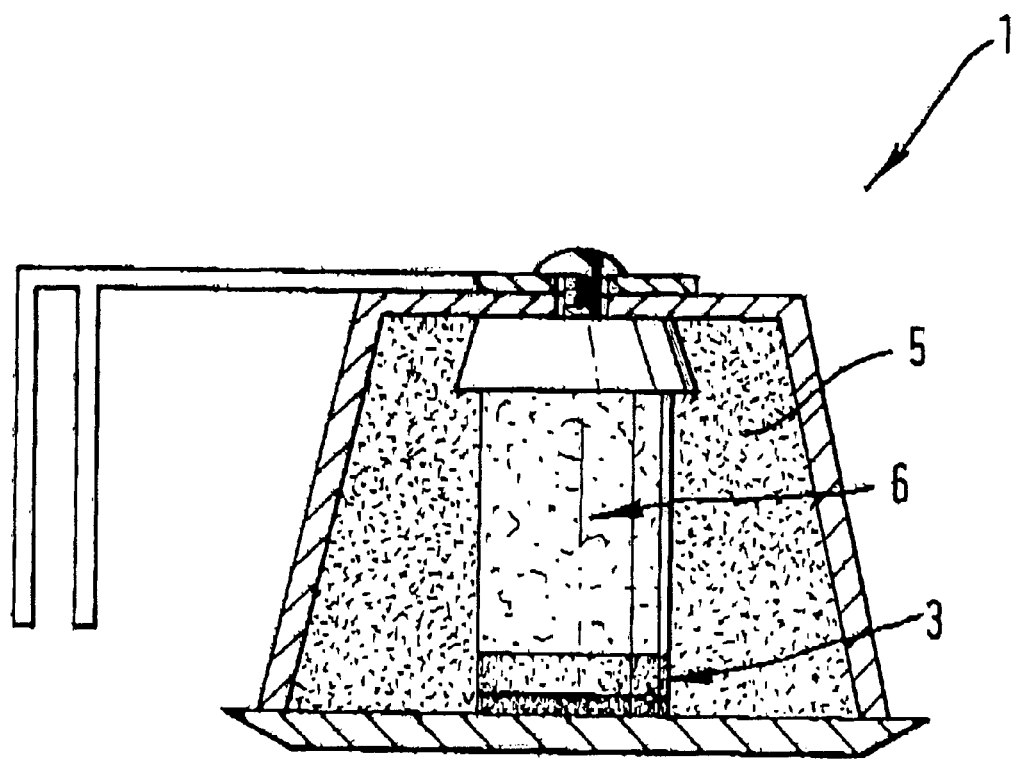
FIG. 1 illustrates a schematic cross sectional view of the device of the invention according to a preferred mode.

The device of the invention is a single unit-dispensing device that delivers an enzymatic cleaning component and a sanitizing agent in a simplified and "manual-free operation". The mechanism is configured as a two-stage device that first releases the enzymatic cleaning component from a first compartment into the reservoir to be cleaned while delaying the release of the sanitizing agent from a second compartment until the surface of the reservoir has been sufficiently cleaned by the enzymatic component. The cleaning component and sanitizing agent are separated by a degradable barrier. The degradable barrier functions to (i) protect the enzyme included in the first compartment from the sanitizing agent that would normally neutralize its effect and (ii) delay the release of the sanitizing agent until after proper cleaning of the surfaces of the reservoir has taken place.

In the present invention, the use of the term "degrade" in connection with the barrier means that the barrier becomes capable of releasing the antimicrobial substance. The barrier may be degraded by any suitable mechanism including, but not limited to, dissolution, enzymatic degradation, chemical degradation, and physical degradation when the barrier is put in contact with an aqueous medium such as water. In the present invention, for sake of simplicity, the term "reservoir" refers to all parts of a food-containing apparatus and may include, without limitations, the container itself; metering means such as an auger; and dispensing means such as a pump, nozzle, seals, hoses, and the like.

The cleaning component of the invention preferably comprises an amount of detergent although the cleaning composition could also be composed of a solution containing one or more enzymes without detergent agent. By "detergent" is meant a synthetic cleansing agent that resembles soap in its ability to emulsify oil and hold dirt and containing surfactants that do not precipitate in hard water as defined in the McGraw-Hill Dictionary Of Scientific And Technical Terms, 5th Edition, edited by Sybil P. Parker, McGraw-Hill Book Co., New York.

Detergents usually contain surfactants that are useful for removing the debris from the surface of the reservoir. These surfactants, however, have a poor effect in removing protein deposits. The protein deposits are typically the cause of opacification and soilage of the reservoir. Therefore, there is a need to combine the detergent with at least one proteolytic agent. Accordingly, the first compartment contains one or more enzymes which can be selectively chosen for their particular proteolytic activities on the residues of food and/or beverage product. The proteolytic enzymes used herein must be at least partially capable of hydrolyzing the amide bonds of peptides in order to degrade the proteinaceous material found on the surface of the reservoir. Additionally, for a number of beverage or food products, it may also be useful to combine the detergent with lipolytic and/or amyolytic agents that are active at degrading lipids and carbohydrates residues, respectively. Accordingly, one or more multi-functional enzymes can be used or, alternatively, separate enzymes such as specifically active lipases or carbohydrases can be used in combination with the proteolytic enzymes.

According to one important aspect of the invention, the enzymatic detergent part and the sanitizing part are separated during storage by a barrier that prevents the one or more enzymes from being destroyed by the effect of the sanitizing agent. The barrier is arranged so that its full integrity is maintained during normal storage conditions of humidity and temperature but is capable of progressively degrading upon exposure to the cleaning conditions.

The barrier may be a mono- or multi layer barrier. In a preferred embodiment of the invention, at least part of the barrier is water-soluble. Preferably, the barrier comprises at least one layer that is water-soluble. In one embodiment, the water soluble layer comprises a sugar-based material. A sugar-based layer is advantageous since it will dissolve slowly when it comes into contact with the aqueous medium of the reservoir. The solubility rate of a sugar-based layer is relatively easy to control and, thus, provides a wide range of solubility rates. The sugar is also physically and bacteriologically stable and relatively chemically neutral.

We have found, however, that it is even more advantageous to have a first outer layer made of the sugar-based material and a second inner support layer made of a second material. The sugar-based material dissolves more slowly in the aqueous liquid than the second material and the second support layer has a relatively higher rigidity than the first layer.

"Inner" and "outer" refer to the relative position of the barrier with respect to the interior of the second compartment that contains the sanitizing agent.

In particular, the second layer is preferably an effervescing agent and provides a large part of the structural and mechanical properties of the barrier and is capable of reacting rapidly with the liquid medium in the reservoir after the first outer layer has dissolved. By effervescing agent is meant an agent that can emit small bubbles of gas. Indeed, it has been found advantageous to have a first sugar-based layer, either soft or rigid, that can sufficiently delay release of the sanitizing agent and a second layer that degrades more rapidly and ensures the strength of the barrier. An effervescing agent as a single layer would dissolve too rapidly and therefore would not be suitable. When the effervescing agent is combined with an outer protective layer, such as a sugar-based layer, however, the layer of effervescing agent is properly protected from moisture ingress and remains in a very stable state over time. Also, the outer layer can be chosen of any suitable texture such as, for example, soft, semi-rigid, or rigid. By using two layers, less importance is placed on obtaining an outer layer that combines both structural and mechanical properties with a suitable solubility rate.

Preferably, the first sugar-based layer has a thickness of about 0.1 mm to 1 mm, more preferably about 0.2 mm to 0.8 mm and the second inner support layer has a thickness of about 0.1 mm to 5 mm, preferably about 0.5 mm to 3 mm, and more preferably about 1 mm to 2 mm. The effervescing material of the support layer is preferably sodium bicarbonate or any equivalent effervescing, relatively inert material.

In another embodiment, the barrier includes at least one layer capable of being degraded by the one or more enzymes included in the first compartment at the time the one or more enzymes are released by the detergent component in the aqueous medium of the reservoir.

In particular at least one layer of the barrier may be of a protein barrier capable of being degraded by a protease. The protease is preferably included in the first compartment for the purpose of degrading proteinous materials attached to the reservoir. The protein layer begins to degrade as a result of the action of the protease at the time the protease is released into the aqueous medium of the reservoir. Appropriate protein material for the barrier includes, but is not limited to, gelatin, corn zein, wheat gluten, milk protein, soy protein, collagen, keratin, peanut protein, and combinations thereof.

In another embodiment, the degradable barrier may be of at least one layer of polysaccharide capable of being degraded by an amylase. Appropriate materials for the polysaccharide layer include, but are not limited to, starch, agar, pectin, sucrose, alginate, chitosan, carrageenan, gums, and combinations thereof. The amylase is useful for cleaning reservoirs that contain high concentrations of carbohydrates in the food or beverage product. Under certain conditions, carbohydrates have a tendency to crystallize on the parts of the reservoir and form undesirable hard residues that are difficult to remove by conventional non-enzymatic detergents.

The barrier can also be made partially, or totally, of cellulose-based material that can be degraded by introducing a cellulase into the cleaning composition. Shellac, which has proved to be slowly degraded by dissolution by alkalies or borax, can also be used for the barrier. Shellac is an insect resinous excretion which is typically used as a coating, for example in a confectionery product.

Of course, depending upon the materials and construction, the barrier may be degraded by both the effects of dissolution in water and the enzymatic reaction of the enzyme present in the aqueous solution after the detergent is released.

In the first compartment of the device, the detergent can be formulated as a dry powder, or solid tablet, or a liquid. Dry powder and tablets are preferred forms because they cause less stability problems for the barrier and may extend the shelf life of the enzymes. When the detergent is liquid, the device has to be adapted accordingly so that the liquid form of the detergent does not interfere with the barrier before application. For instance, the compartment of the detergent and the compartment of the antimicrobial agent may positioned together so as to form a side-by-side arrangement.

The detergent is preferably an alkaline medium which is necessary to increase the efficiency of soil removal and sediment breakdown. The alkaline medium also permits the use enzymes that remain active under alkaline conditions and which are more commonly available and less expensive than enzymes which are active under neutral or acidic conditions.

Detergents include, but are not limited to, alkali-metal hydroxides, carbonates, silicates, phosphates, sulfites, and mixtures thereof. Preferred alkali-metal hydroxides are potassium hydroxide, sodium hydroxide, lithium hydroxide, calcium hydroxide, and mixtures thereof. Preferred carbonates are alkali metal carbonates including, but not limited to, sodium carbonate, potassium carbonate, sodium and potassium carbonates, or sesquicarbonate. Phosphates that may be used as an alkalinity source include, among others, cyclic phosphates and alkaline condensed phosphates. Phosphates are preferred for use with the invention. Sulfites may advantageously be added to the detergent composition to reduce corrosion of metal parts in the reservoir.

Examples of suitable proteolytic enzymes which may be utilized in the cleaning composition include, but are not limited to, trypsin, pepsin, subtilisin, proteinase, and mixtures thereof. A suitable example of a protease is proteinase from bacterial origin such as subtilisin carlsberg obtained from *Bacillus licheniformis* . An example of a lipase is lipolase derived from *Aspergillus oryzae* commercialized by Novo Nordisk, Inc. An example of an amylase is Fungamyl 800 commercialized from Novo Nordisk, Inc.

It has been found that the device of the invention may advantageously be used to clean and sanitize reservoirs for "granita" products that usually contain coffee, milk powder, sugar, and the like in their formulations. For such products it can be important to include proteinase(s) and lipase(s) to attack milk proteins and fats, respectively. Sugar is usually readily soluble in water and, thus, the use of carbohydrase is not absolutely necessary for cleaning purpose, however, its use is not excluded and carbohydrase may optionally be used in some circumstances.

By "clean" or "cleanse" is meant that dirt, food or beverage debris, sediment, and impurities that are deposited on the surfaces of the reservoir are removed and that the surface of the reservoir is unsoiled.

The second compartment of the device preferably comprises a dry antimicrobial part used to sanitize the food or beverage reservoir. The antimicrobial part may be in any form including, but not limited to, powder, granular, and compressed block forms.

The one or more anti-microbial agents are utilized in an amount effective to eliminate substantially or to reduce significantly the number of viable microorganisms found on the surfaces of the reservoir. In general, a reservoir is considered as microbiologically sanitized when the remaining bacteria population does not exceed about 100 cfu/cm$^2$. For instance, it has been found that an amount of available chlorine from about 100 ppm to 200 ppm is generally effective to properly sanitize a beverage reservoir.

In a preferred embodiment, the second compartment comprises a substance having an anti-microbial activity of relatively large spectrum. Appropriate anti-microbial agent include chlorine-based compounds or quaternary ammonium compounds that do not affect the integrity of the barrier (i.e., in particular, that they do not react with the sodium bicarbonate tablet when it is used as an inner layer of the barrier). Chlorine has antimicrobial activity and is fairly inexpensive. Under strong concentrations and/or inappropriate sanitizing times (e.g., overnight applications), however, chlorine can be very corrosive to metals. Quaternary ammonium compounds are non-corrosive and, thus, are preferred when the sanitizing agent contacts metal parts. Quaternary ammonium compounds also leave very little after-taste and are chemically friendly. Quaternary ammonium compounds, however, usually do not have as broad an antimicrobial spectrum as chlorine-based sanitizers. By quaternary ammonium compounds is meant any organic nitrogen containing compound wherein at least one nitrogen atom is tetravalent (i.e., has four bonds to substituent groups). Of course, any other suitable sanitizers may be included depending upon the need to kill specific germs and bacteria. Examples of preferred sanitizers include, but are not limited to, chloramine T, benzalkonium chloride, sodium dichloroisocyanurate, calcium hypochlorite, and mixtures thereof.

The device of the invention is installed within or along the edges of the reservoir after the reservoir has been filled with water. The first compartment preferably comprises at least one opening adapted to release the enzymatic detergent within the reservoir by the effect of gravity when the device is positioned in the reservoir so that the at least one opening of the compartment is directed downward. The opening may be closed by a removable lid or may be closed by a selective filtering means that prevents the composition from exiting the compartment before the device at least partially contacts water.

In a preferred embodiment of the invention, the first compartment includes a housing adapted to receive the second compartment. When the lid for closing the opening of the first compartment is removed the barrier becomes exposed and comes into direct contact with the aqueous medium in the reservoir. Therefore, at the same time the detergent is released, the barrier begins to degrade and continues degrading until the anti-microbial component is finally released.

The device may advantageously comprise a means for connecting the device to the reservoir in a position that is adapted to sufficiently exposure the barrier to the aqueous medium. Preferably, it is a means for hanging the device on the edge of the reservoir or a means for adhesively attaching the device to the interior of the reservoir. The device may be positioned so as to be entirely or partially immersed in the aqueous medium. The important factor is to always have the barrier entirely immersed in the aqueous medium.

Figure 2:
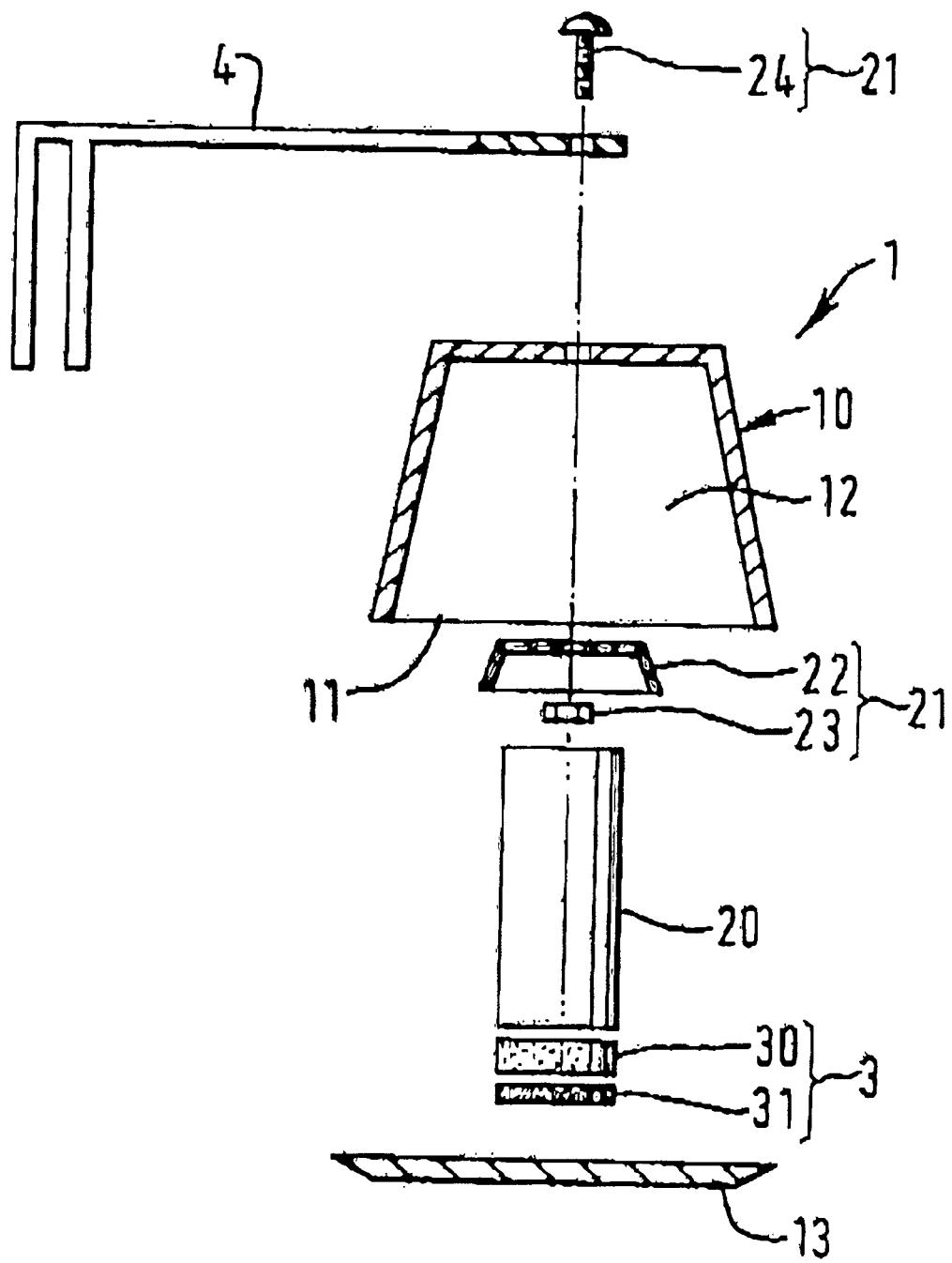
FIG. 2 is an exploded view of the device of FIG. 1.

As illustrated in FIG. 1 and FIG. 2, device 1 comprises a cup 10 with a large lower opening 11 and a housing 12. Housing 12 is large enough to receive an inner tubular portion 20 of hollow configuration. Portion of tube 20 is attached by its upper end at the bottom of the cup by suitable connecting means 21 such as cap 22 and a nut 24 and bolt 23 assembly. A hanging portion 4 is provided at the top of the cup and connected to the top by means of the nut 24 and bolt 23 assembly that goes through the cup. The lower portion of the inner compartment 20 is imperviously closed by a dissolving barrier 3. In the preferred example, barrier 3 includes an inner sodium bicarbonate tablet 30 and an outer sugar-based layer 31. For instance, the sugar-based layer may be made of 20 g sucrose and 10 g high fructose corn syrup. The dissolving barrier 3 is dimensioned to entirely dissolve approximately 30 min after being dipped in cold water. A removable lower lid 13 is provided to close the cup before the device is in use.

As shown in FIG. 1, a first compartment is defined in the housing by the walls of cup 10 and the walls of the tube 20 so as to offer sufficient room for enzymatic detergent 5 to be placed in the first compartment. The sanitizing or antimicrobial agent 6 is located within the inner portion of tube 20. The enzymatic detergent is separated from the detergent by the barrier or membrane 3.

FIG. 3 illustrates the method for cleaning and sanitizing a food or beverage reservoir according to the invention. The reservoir is first pre-rinsed with water. The device is then opened to allow the detergent to be dispensed into the reservoir filled with potable water 16 and the device 1 is clipped onto the side 7 of the reservoir and the dissolving barrier 3 is allowed to come in contact with the detergent solution. Once engaged, the dissolving barrier slowly dissolves over a period of about 25–35 min, thereby, allowing the sanitizer 6 to be released after the enzymatic detergent has completed cleansing the reservoir. The sanitizer is allowed to work for about an additional 15 minutes. The reservoir is then drained and rinsed with potable water.

The main advantages of cleaning and sanitizing a food or beverage reservoir with the device of the invention is that it allows the operator to reduce his/her involvement in the cleaning and sanitizing procedures. The cleaning protocol is simplified and the device allows the operator to be minimally involved with the cleaning procedure. Thus, the frequency and time of cleaning the beverage-dispensing machines can be easily adapted to the needs of the operator. For example, since attendance of an individual is not required, the device can be used at the end of a working day and the cleaning process completed on the following day. Similarly, since there is very little need for an individual to physically clean the reservoir the person can be redirected to other duties. Furthermore, the device also improves cleaning practices by providing a consistent cleaning procedure; avoids having to completely disassemble or dismantle all of, or part of, the reservoir; and reduces exposure of the operator to the active ingredients.

The word "about," as used herein, is intended to refer to both numbers in any range of numbers.

EXAMPLE

The following example is merely illustrative and is not intended to limit the scope of the invention.

A cleaning and sanitizing cartridge according to the invention was used to clean a beverage dispensing machine. The composition of the detergent was a homogeneous blend of sodium linear alkylaryl sulfonate, phosphates, carbonates, and a protease enzyme (from bacterial origin; i.e., *Bacillus licheniformis* sp. subtilisin carlsberg). The detergent/enzyme weight was 60 g. The sanitizer was 7 g of a chlorine based chemical (i.e., dichloro isocyanuric acid, sodium salt). The barrier consisted of an effervescent tablet and a sugar coating. The effervescent tablet consisted of sodium bicarbonate and citric acid. The tablet had a diameter of 2.5 cm and thickness of 0.3 cm. The sugar layer consisted of high fructose corn syrup and sucrose in a ratio of 2:1. The sugar mixture was melted to a thick syrup and poured onto the tablet to completely cover one side of the tablet. The thickness of the sugar layer was between 0.3 and 0.5 cm.

A beverage dispensing machine that produces "iced" coffee drinks known as a Bunn machine (15-liter capacity) had been soiled with a coffee beverage at two different levels (heavily soiled and moderately soiled). The level of bacteria was counted in a reference area on the food contact surface. The counting method involved taking a prewetted swab and sampling an area about 10 cm×10 cm with the swab before and after cleaning the device. The swab was then placed into a diluent (i.e., 0.1% peptone) and agitated to dislodge any bacteria on the swab. An aliquot (usually 0.1 mL) was taken from the diluent and dispensed onto a petri plate containing solid growth medium of the type "Standard Plate Count Media" (commercially available from Difco of Detroit, Mich.). The plates were incubated at 30° C. for 1–2 days. If a bacterium is present, the microorganisms develop into a colony on the petri plate that can be seen with the naked eye. The colonies are visually counted and reported as the number of colony forming units relative to the surface area that was sampled (i.e. $cfu/cm^2$).

The following results were obtained:

TABLE 1

First trial of cleaning a beverage dispenser (Bunn) using the two stage cleaning device (heavily soiled)

| Type of surface | Before treatment ($cfu/cm^2$) | After treatment ($cfu/cm^2$) |
| --- | --- | --- |
| Left wall of reservoir | 11000 | <100 |
| Right wall of reservoir | 160000 | <100 |
| Front wall | 150000 | <100 |
| Barrel end | 58000 | <100 |
| Seal | 55000 | 100 |
| Nozzle wall | 120000 | 130000 |
| Auger | 51000 | 1100 |
| Base | 90000 | <100 |
| Cooling tube (in) | 120000 | <100 |
| Cooling tube (out) | 130000 | <100 |

TABLE 2

Second trial of cleaning a beverage dispenser (Bunn) using the two stage cleaning device (moderately soiled)

| Type of surface | Before treatment ($cfu/cm^2$) | After treatment ($cfu/cm^2$) |
| --- | --- | --- |
| Left wall of reservoir | 100 | <100 |
| Right wall of reservoir | 200 | <100 |
| Front wall | 200 | <100 |
| Barrel end | 1600 | <100 |

TABLE 2-continued

Second trial of cleaning a beverage dispenser (Bunn)
using the two stage cleaning device (moderately soiled)

| Type of surface | Before treatment (cfu/cm$^2$) | After treatment (cfu/cm$^2$) |
| --- | --- | --- |
| Seal | <100 | <100 |
| Nozzle wall | 1400 | 1000 |
| Auger | <100 | <100 |
| Base | <100 | <100 |
| Cooling tube (in) | <100 | <100 |
| Cooling tube (out) | <100 | <100 |

The results show that the device of the invention effectively cleanses and sanitizes the Bunn beverage dispenser.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A device for cleaning and sanitizing a beverage or food reservoir comprising:
    a first compartment containing a cleaning component comprising at least one or more enzymes in an amount sufficient to cleanse the reservoir; and
    a second compartment comprising at least one antimicrobial substance in an amount sufficient to sanitize the reservoir,
    wherein the first compartment and the second compartment are separated by a barrier that degrades upon contact with an aqueous medium and that delays the release of the antimicrobial substance from the second compartment until after the cleaning component has cleansed the reservoir.

2. The device of claim 1, wherein the degradable barrier is soluble in the aqueous medium.

3. The device of claim 2, wherein the degradable barrier comprises one or more layers and at least one layer comprises a sugar-based material.

4. The device of claim 3, wherein the degradable barrier includes a first outer layer made of the sugar-based material and a second inner support layer made of a second material, wherein the first outer layer dissolves more slowly in the aqueous medium than the second inner support layer and wherein the second inner support layer is more rigid than the first layer.

5. The device of claim 4, wherein the second inner layer is effervescent.

6. The device of claim 1, wherein the barrier includes at least one layer capable of being degraded by one or more of the enzymes included in the first compartment after the one or more enzymes are released into the aqueous medium.

7. The device of claim 6, wherein the barrier comprises a protein capable of being degraded by a protease.

8. The device of claim 6, wherein the barrier comprises a polysaccharide capable of being degraded by an amylase.

9. The device of claim 1, wherein the first compartment comprises at least one opening to dispense the cleaning component into the reservoir by gravity when the device is positioned in the reservoir so that the opening is directed downward.

10. The device of claim 9, further comprising a removable lid attached to the opening to prevent the cleaning component from exiting the opening until after the lid is removed.

11. The device of claim 10, wherein the first compartment is defined by a plurality of walls of a housing and an inner tube having at least one wall that is attached to the housing, the second compartment is defined by an interior of the inner tube, and the barrier is exposed to and can contact the aqueous medium after the lid is removed.

12. The device of claim 9, further comprising a means for hanging the device on the edge of the reservoir so that the opening faces downward.

13. The device of claim 1, wherein the cleaning component further comprises one or more detergents selected from the group consisting of alkali metal hydroxides, carbonates, silicates, phosphates, sulfites, and mixtures thereof.

14. The device of claim 1, wherein the one or more enzymes is selected from the group consisting of amylases, proteases, lipases, and mixtures thereof.

15. The device of claim 1, wherein the antimicrobial agent comprises chlorine, a quaternary ammonium compound, or a combination thereof.

16. The device of claim 1, wherein the barrier is adapted to release the antimicrobial composition into the reservoir after about 15 to 40 minutes following the release of the detergent.

17. The device of claim 16, wherein the barrier is adapted to release the antimicrobial composition into the reservoir after about 25 to 35 minutes following the release of the detergent.

18. A method for cleaning and sanitizing a beverage or food reservoir comprising:
    filing the reservoir with water;
    placing the device of claim 1 in the reservoir so that the cleaning component is released from the first compartment, the barrier is at least partially immersed in the water, and the antimicrobial substance is released from the second compartment to cleanse and sanitize the reservoir after the barrier degrades sufficiently; and
    draining the water solution after the antimicrobial agent has sanitized the reservoir.

19. The method of claim 18, wherein the device is placed in the reservoir for about 30 to 60 minutes.

20. The method of claim 19, wherein the device is placed in the reservoir for about 25 to 45 minutes.

* * * * *